US011684383B2

(12) United States Patent
Richards et al.

(10) Patent No.: US 11,684,383 B2
(45) Date of Patent: Jun. 27, 2023

(54) DISTALLY GENERATED ULTRASONIC MOTION RESECTION TOOL

(71) Applicant: Boston Scientific Scimed, Inc., Maple Grove, MN (US)

(72) Inventors: Laura E. Richards, Worcester, MA (US); Kyla Killinger, Denver, CO (US); Kirsten Linnabary, Gahanna, OH (US); James J. Scutti, Norwell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 280 days.

(21) Appl. No.: 17/082,515

(22) Filed: Oct. 28, 2020

(65) Prior Publication Data

US 2021/0121195 A1 Apr. 29, 2021

Related U.S. Application Data

(60) Provisional application No. 62/927,427, filed on Oct. 29, 2019.

(51) Int. Cl.
*A61B 17/32* (2006.01)
*B06B 1/06* (2006.01)
*A61B 17/00* (2006.01)

(52) U.S. Cl.
CPC ............. *A61B 17/320068* (2013.01); *A61B 17/32002* (2013.01); *B06B 1/0611* (2013.01);
(Continued)

(58) Field of Classification Search
CPC .......... A61B 17/320068; A61B 2017/320071; A61B 17/32002; A61B 2017/320077;
(Continued)

(56) References Cited

U.S. PATENT DOCUMENTS 6,063,098 A * 5/2000 Houser ............... B06B 3/00
606/169
6,454,782 B1 * 9/2002 Schwemberger ............
A61B 17/320068
606/174
(Continued)

FOREIGN PATENT DOCUMENTS

EP 3453309 A1 3/2019
WO 2010045158 A2 4/2010

OTHER PUBLICATIONS

"Bertke BD, Scoggins P, Welling AL, Widenhouse T, Chen C, Kallakuri S, Cavanaugh JM, Clymer J, Amaral J. Ex vivo and in vivo evaluation of an ultrasonic device for precise dissection, coagulation, and transection. Open Access Surgery. 2015;8:1-7 https://doi.org/10.2147/OAS.S73851".
(Continued)

*Primary Examiner* — Kathleen S Holwerda
*Assistant Examiner* — Serenity A Miller
(74) *Attorney, Agent, or Firm* — Seager, Tufte & Wickhem, LLP

(57) ABSTRACT

The present disclosure relates generally to the field of medical devices. In particular, the present disclosure relates to endoscopic medical devices with distally actuated axial displacement configured to impart in-plane or rotational ultrasonic reciprocation to an end effector.

7 Claims, 8 Drawing Sheets

(52) U.S. Cl.
CPC ........... *A61B 2017/00402* (2013.01); *A61B 2017/320028* (2013.01); *A61B 2017/320077* (2017.08); *A61B 2017/320082* (2017.08); *B06B 2201/76* (2013.01)

(58) Field of Classification Search
CPC .......... A61B 2017/320082; A61B 17/320016; A61B 17/2202; A61B 17/22012; A61B 17/28–295; B26B 7/00
USPC ....................................................... 606/169
See application file for complete search history.

(56) References Cited

U.S. PATENT DOCUMENTS

| | | | |
|---|---|---|---|
| 9,408,622 B2* | 8/2016 | Stulen | A61B 18/1447 |
| 10,022,142 B2* | 7/2018 | Aranyi | A61B 17/320092 |
| 2009/0112229 A1* | 4/2009 | Omori | A61B 34/70 |
| | | | 606/205 |
| 2012/0101512 A1 | 4/2012 | Locke et al. | |
| 2013/0190758 A1* | 7/2013 | Smith | A61B 17/320016 |
| | | | 606/47 |
| 2014/0005705 A1* | 1/2014 | Weir | A61B 18/08 |
| | | | 606/169 |

OTHER PUBLICATIONS

International Search Report and Written Opinion for the International Patent Application No. PCT/US2020/057646, dated Feb. 10, 2021, 24 pages.

* cited by examiner

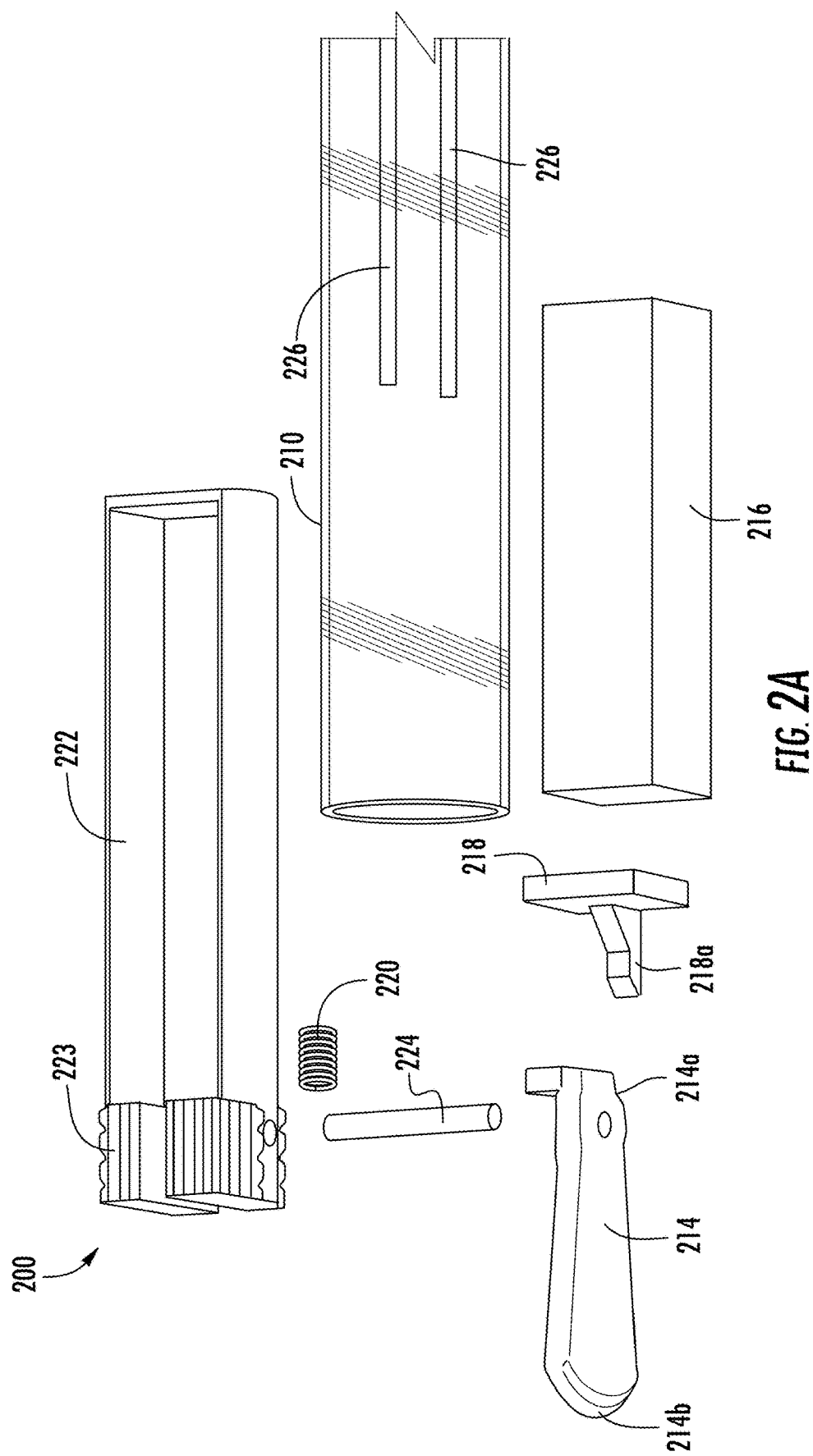

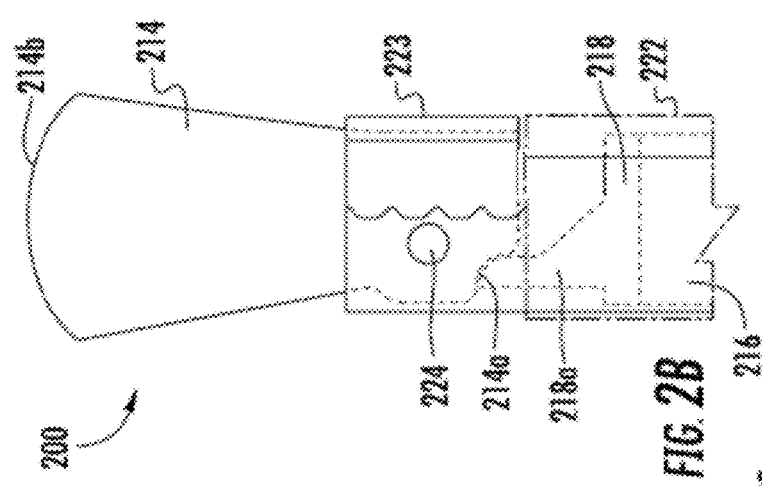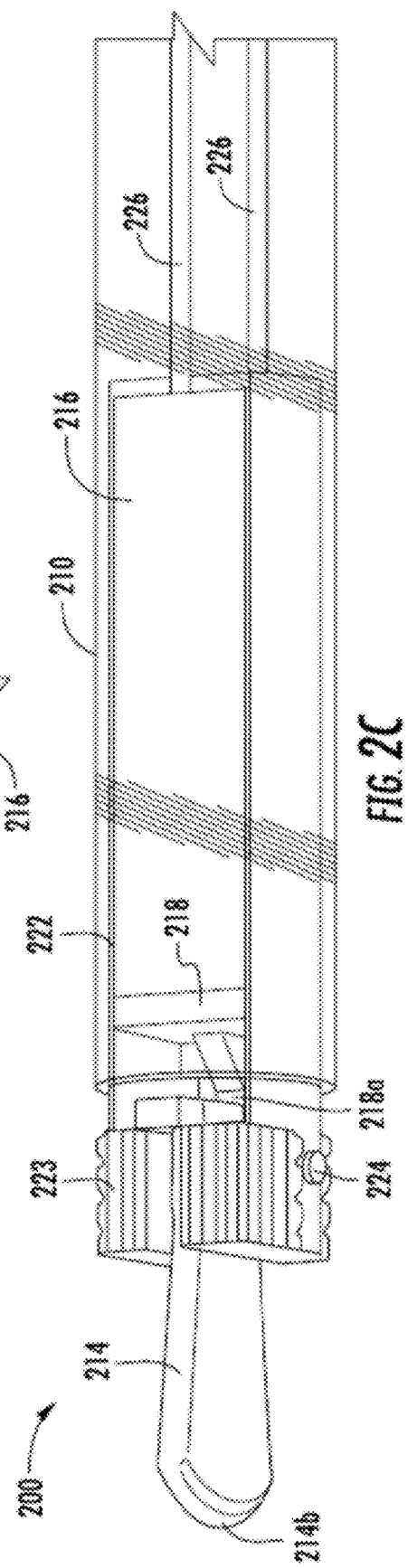

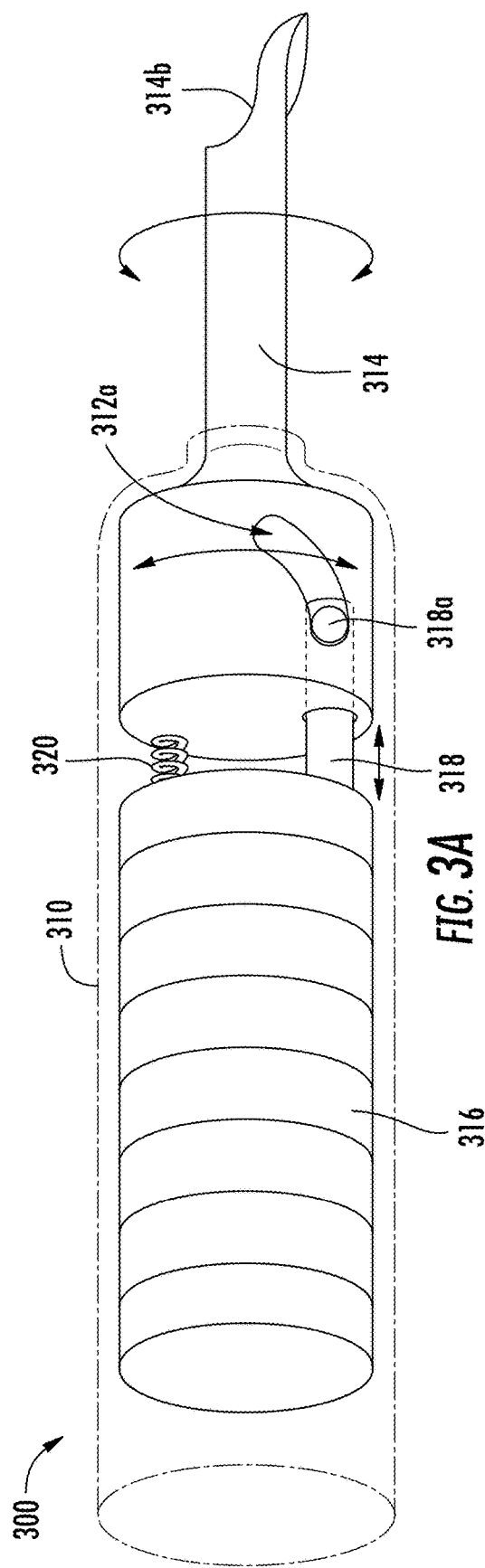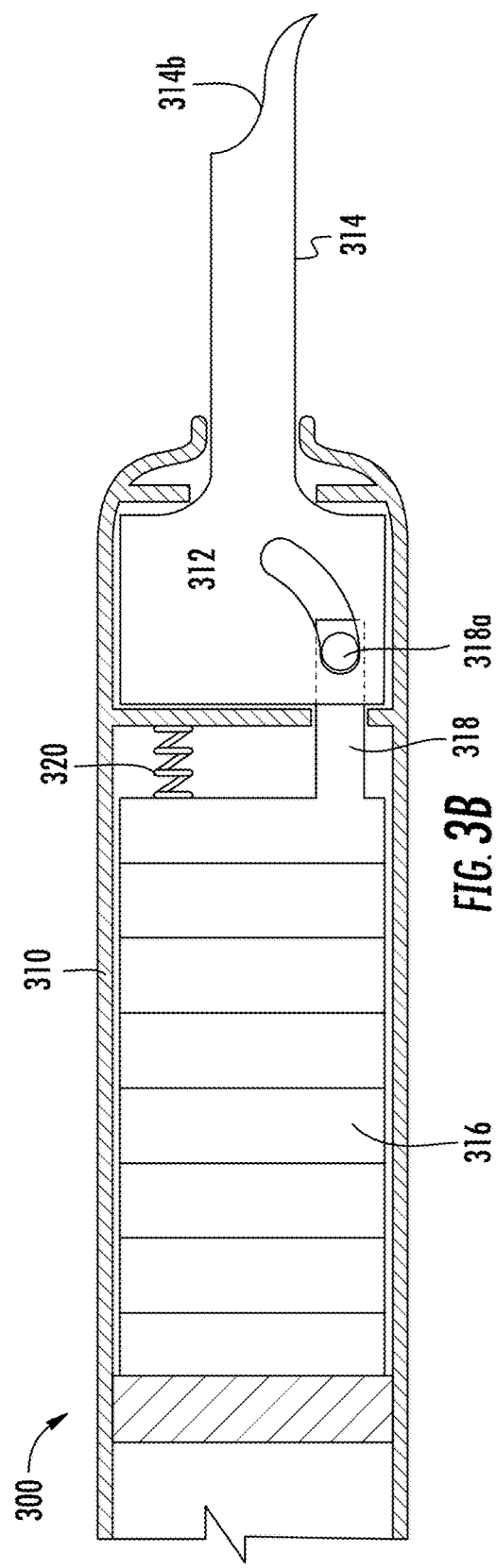

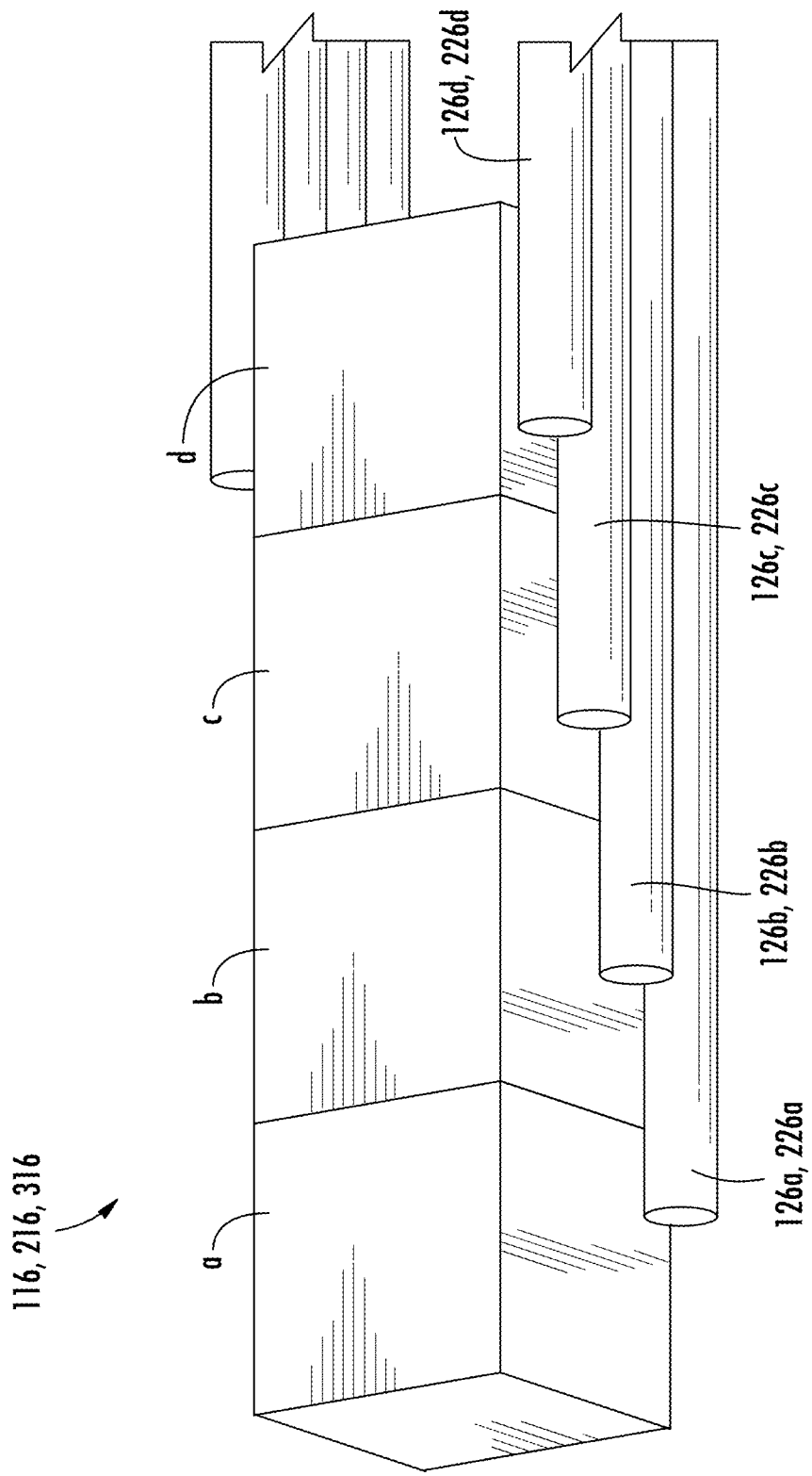

DISTALLY GENERATED ULTRASONIC MOTION RESECTION TOOL

RELATED APPLICATIONS

This application claims the benefit of priority under 35 U.S.C. § 119 to U.S. Provisional Application No. 62/927,427, titled "Distally Generated Ultrasonic Motion Resection Tool", filed on Oct. 29, 2019, the entirety of which is incorporated herein by reference.

FIELD

The present disclosure relates generally to the field of medical devices. In particular, the present disclosure relates to endoscopic medical devices with distally actuated axial displacement configured to impart in-plane or rotational ultrasonic reciprocation to an end effector.

BACKGROUND

Optimal endoscopic resection of a target tissue should cause minimal damage to both the resected tissue (e.g., for accurate post-operative diagnosis and visualization of the tissue margins to verify complete removal) and the surrounding tissue architecture (e.g., to minimize post-operative complications). The heat generated by conventional radiofrequency (RF) energy tissue resection devices, which is necessary to promote coagulation and control bleeding, tends to damage/destroy the architecture of both the target tissue and the healthy surrounding tissue.

A variety of advantageous medical outcomes may therefore be realized by the ultrasonic endoscopic medical devices of the present disclosure.

SUMMARY

In one aspect, the present disclosure relates to an ultrasonic medical device comprising a flexible elongate sheath. A collar may be attached to a distal end of the flexible elongate sheath. An end effector may be pivotally attached to the collar. A transducer may be housed within a distal portion of the flexible elongate sheath. A motion block may be housed within the distal portion of the flexible elongate sheath and between the transducer and the end effector. An arm of the motion block may be configured to move along a curved surface of the end effector. A compression spring may be disposed between the motion block and a proximal end of the end effector.

In the above-described and other embodiments, the compression spring may contact a distal end of the motion block and the proximal end of the end effector. The transducer may be configured to translate linear motion to the motion block. The arm of the motion block may be configured to move along the curved surface of the end effector to translate in-plane reciprocating movement to the end effector. The transducer may be configured to move the arm of the motion block distally along the curved surface of the end effector. The compression spring may be configured to move the arm of the motion block proximally along the curved surface of the end effector. A lead may extend along a full length of the flexible elongate sheath. A proximal end of the lead may be connected to an energy source and a distal end of the lead may be connected to the transducer. The transducer may include a stack of piezoelectric disks in parallel.

In another aspect, the present disclosure relates to an ultrasonic medical device comprising a flexible elongate sheath. A sling may be disposed within a distal portion of the flexible elongate sheath. The sling may include a reflow element extending beyond a distal end of the flexible elongate sheath. An end effector may be pivotally attached to the reflow element by a pin. A transducer may be housed within a distal portion of the flexible elongate sheath. A motion block may be housed within the distal portion of the flexible elongate sheath and between the transducer and the end effector. An arm of the motion block may be configured to move along a curved surface of the end effector. A torsion spring may be disposed around the pin within the reflow element.

In the above-described and other embodiments, the torsion spring may be configured to move between a non-compressed configuration and a compressed configuration around the pin. The transducer may be configured to translate linear motion to the motion block. The arm of the motion block may be configured to move along the curved surface of the end effector to translate in-plane reciprocating movement to the end effector. The transducer may be configured to move the arm of the motion block distally along the curved surface of the end effector. The torsion spring may be configured to move the arm of the motion block proximally along the curved surface of the end effector. A lead may extend along a full length of the flexible elongate sheath. A proximal end of the lead may be connected to an energy source and a distal end of the lead may be connected to the transducer. The transducer may include a stack of piezoelectric disks.

In yet another aspect, the present disclosure relates to an ultrasonic medical device comprising a flexible elongate sheath. A tubular end effector may be disposed within a distal portion of the flexible elongate sheath. A transducer may be housed within the distal portion of the flexible elongate sheath and proximal to the tubular end effector. An actuator rod may be disposed within the distal portion of the flexible elongate sheath and between the tubular end effector and transducer. A distal end of the actuator rod may be configured to move along a curved slot formed within the tubular end effector. A compression spring may be disposed between the wall within the flexible shaft and the transducer. A cutting edge or other functional characteristic or shape may be attached to a distal end of the tubular end effector. The tubular end effector may comprise a hypotube or a fabrication of hypotubes of varying diameters and wall thicknesses.

In the above-described and other embodiments, the compression spring may contact a distal end of the transducer and an inner wall of the tubular end effector proximal to the end effector. The transducer may be configured to translate linear motion to the actuator rod. The distal end of the actuator rod may be configured to move along the curved slot of the tubular end effector to translate rotational reciprocating movement to the end effector. The transducer may be configured to move the distal end of the actuator rod distally along the curved slot of the tubular end effector. The compression spring may be configured to move the distal end of the actuator rod proximally along the curved slot of the tubular end effector. A lead may extend along a full length of the flexible elongate sheath. A proximal end of the lead may be connected to an energy source and a distal end of the lead may be connected to the transducer.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 2A-2C provide perspective views of an ultrasonic endoscopic medical device, according to one embodiment of the present disclosure.

FIGS. 3A-3B provide perspective views of an ultrasonic endoscopic medical device, according to one embodiment of the present disclosure.

FIG. 5 provides a perspective view of a piezoelectric transducer, according to one embodiment of the present disclosure.

DETAILED DESCRIPTION

Figure 1A:
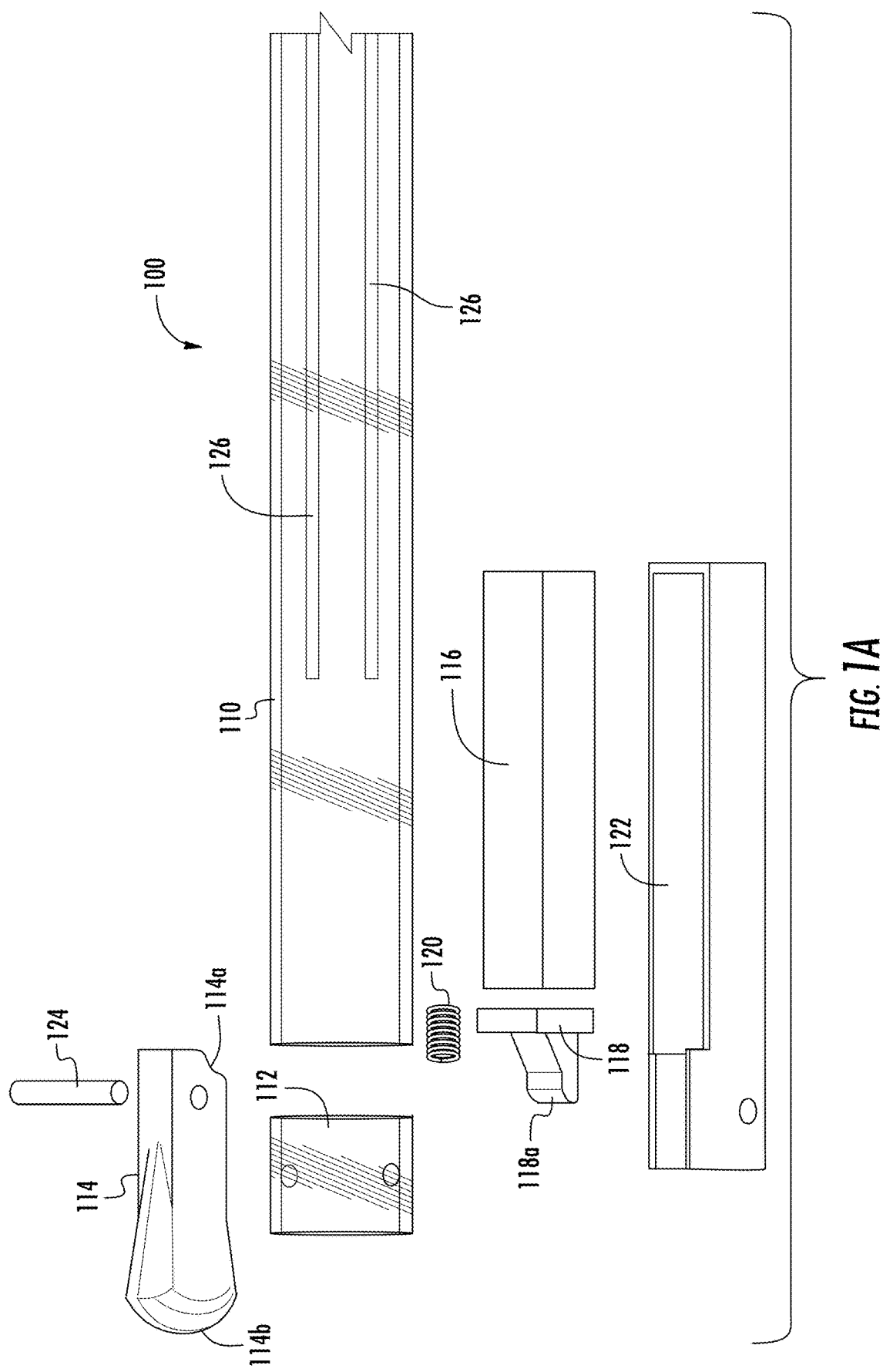
FIGS. 1A-1F provide perspective views of an ultrasonic endoscopic medical device, according to one embodiment of the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with reference to ultrasonic endoscopic medical devices, e.g., which include distally actuated end effectors configured to cut/resect mucosal tissue of the gastrointestinal (GI) tract using ultrasonic transverse rotation, it should be appreciated that such ultrasonic endoscopic medical devices may include a variety of end effectors (e.g., scissors, graspers, biopsy needles, etc.) configured to manipulate mucosal and non-mucosal tissues in a variety of body lumens, body passageways, organs and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional or physician when introducing a device into a patient, while the term "proximal" refers to the end closest to the medical professional or physician when introducing a device into a patient.

An obstacle to the development of endoscopic medical devices with ultrasonic end effectors is the generation and translation of motion along the length of the endoscopic medical device, which typically includes a flexible elongate member, to a distal end effector. Translating the motion along the length of the endoscopic medical device without generating excessive heat adds further complexity to the obstacle. Laparoscopic medical devices used for open surgical procedures (e.g., non-endoscopic devices) are sufficiently large to include a transducer in a handle that is rigidly connected to a distal amplification horn and/or the distal end effector to support the translation of linear actuation to impart ultrasonic motion in the distal end effector. However, in current endoscopic medical devices, the translation of linear motion to a distal amplification horn is challenging due to flexibility and sizes of the current endoscopic medical devices. In various embodiments, the present disclosure relates generally to flexible endoscopic medical devices which may use distally actuated axial displacement to impart in-plane ultrasonic reciprocation (e.g., ultrasonic transverse rotation, etc.) to an end effector without the need for a distal amplification horn. As described herein, the low temperature frictional heat induced by such ultrasonic transverse rotation may allow the end effector to cut and coagulate tissue with high precision (e.g., along the desired tissue margins) without damaging/destroying tissue architecture (e.g., of the target tissue and/or the surrounding tissues). In various embodiments, an end effector of the present disclosure may include a variety of cutting surfaces and/or profiles, including, by way of non-limiting example, a sharpened edge, a serrated edge, a semi-sharpened edge, a dulled edge, a curved edge, a scalloped edge and combinations thereof.

Figure 1D:
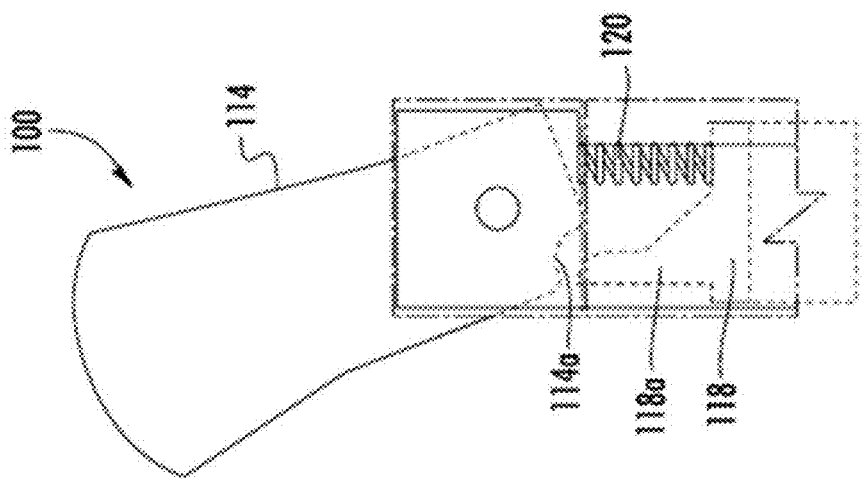
Figure 1C:
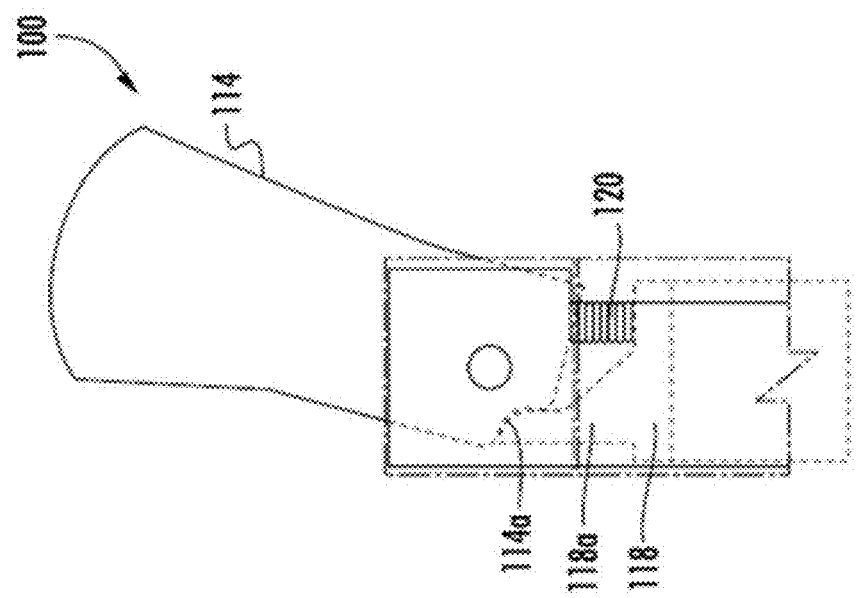
Figure 1B:
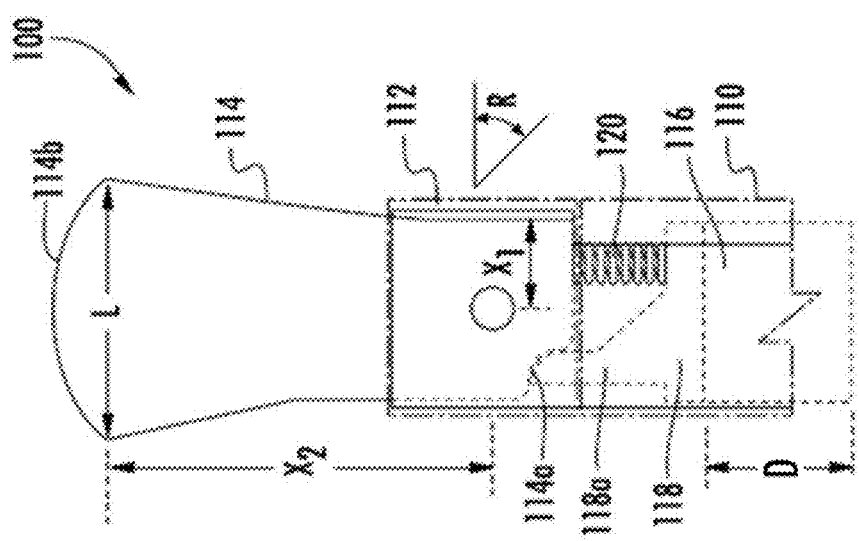
Figure 1E:
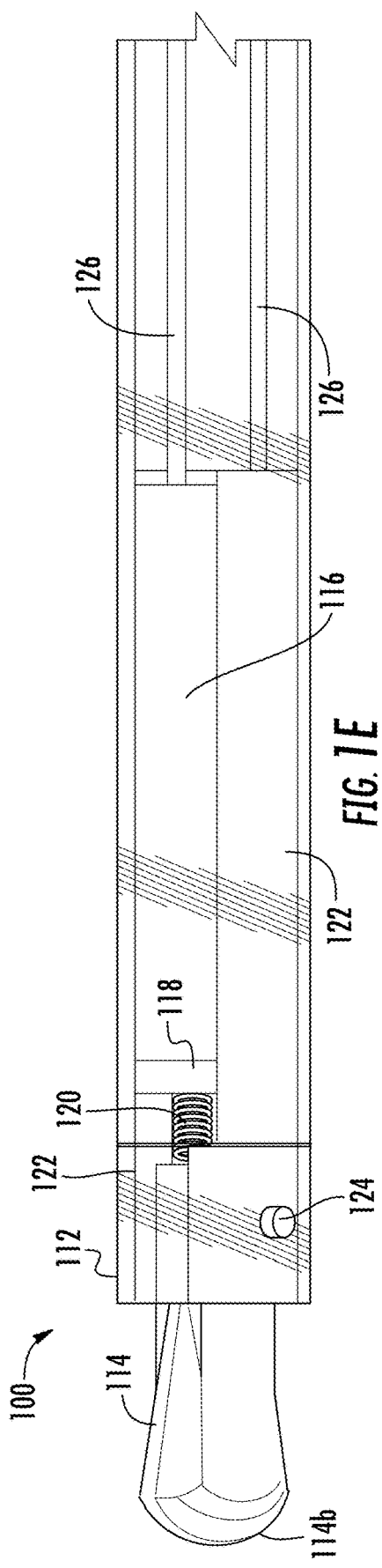
Figure 1F:
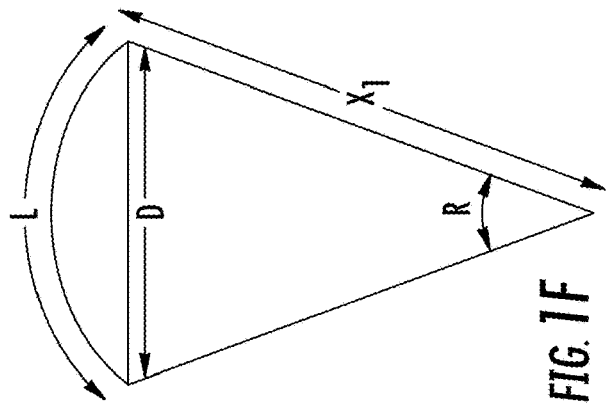

Referring to FIGS. 1A-1F, in one embodiment, an ultrasonic medical device 100 of the present disclosure may include a collar 112 attached to a distal end of a flexible elongate sheath 110 (e.g., catheter, etc.). An end effector 114 (e.g., blade, etc.) may be pivotally attached to the collar 112 such that a cutting edge 114b of the end effector 114 may extend beyond a distal end of the collar 112. A transducer 116 (e.g., one or more piezoelectric stacks/disks) may be housed within a distal portion of the flexible elongate sheath 110. A motion block 118 may be housed within the distal portion of the flexible elongate sheath 110 and between the transducer 116 and the end effector 114. An arm 118a (e.g., distal arm) of the motion block 118 may be configured to move along (e.g., slide along) a curved surface 114a of the end effector 114. In various embodiments, the curved surface 114a may be disposed along one side of a proximal portion of the end effector 114 and may extend into the distal portion of the flexible elongate sheath 110. A compression spring 120 (e.g., pre-load device, etc.) may be disposed between the motion block 118 and a proximal end of the end effector 114. For example, the compression spring 120 may be disposed adjacent to (e.g., alongside) the arm 118a of the motion block 118 within a space between a distal end of the motion block 118 and a proximal end of the end effector 114. As discussed below, the compression spring 120 may move from a substantially non-compressed (e.g., relaxed) configuration to a compressed configuration as the end effector 114 moves/pivots away from a first position (see e.g., FIG. 1D) to a second position (see e.g., FIG. 1C). In some embodiments, the first position may comprise a home or resting position.

In one embodiment, the collar 112 may be attached to the flexible elongate sheath 110 by a sling 122. For example, a proximal portion of the sling 122 may be housed within the distal portion of the flexible elongate sheath 110 and a distal portion of the sling 122 may be housed within the collar 112. The end effector 114 may be pivotally attached to the collar 112 by a pin or lever arm 124 extending through opposite sides of the collar 112 and sling 122 and through a proximal portion of the end effector 114. In various embodiments, the transducer 116, motion block 118 and compression spring 120 may be housed within the proximal portion of the sling 122, e.g., within the distal portion of the flexible elongate sheath 110. One or more leads 126 (e.g., flexible control wire(s), flexible signal wire(s), etc.) may extend along a length of the flexible elongate sheath 110 (e.g., along an inner or outer surface of the flexible elongate sheath). A proximal end of the lead(s) 126 may be connected to (e.g., conductively or electrically connected to) an external energy source (e.g., a RF generator, not shown) and a distal end of the lead(s) 126 may be conductively connected to the transducer 116.

In one embodiment, the transducer 116 (e.g., when energized by the external energy source) may be configured to translate (e.g., impart) linear motion (e.g., linear displacement, linear movement, etc.) to the motion block 118 relative to a longitudinal axis of the flexible elongate sheath 110. The arm 118a of the motion block 118 may be configured to move along the curved surface 114a of the end effector 114 to translate (e.g., impart) a side-to-side reciprocating movement (e.g., displacement in-plane) to the end effector 114, e.g., as the end effector 114 pivots around the pin 124. The combined interactions of the transducer 116, the motion block 118, the end effector 114 and the compression spring 120 may translate axial displacement of the motion block 118 by the transducer 116 to side-to-side reciprocation in-plane of the end effector 114. As discussed below, the interaction between the arm 118a of the motion block 118 and the curved surface 114a of the end effector 114 may provide angular displacement through varying radial lengths ($X_1$ in FIG. 1B) to amplify in-plane displacement of the distal end of the end effector 114, e.g., to provide ultrasonic in-plane reciprocal movement. One embodiment for the end effector is a cutting blade. When the blade is reciprocating side-to-side and the device is advanced to contact tissue, the target tissue will be cut.

In various embodiments, the combined interaction of the transducer 116 and motion block 118 may be configured to move/pivot the end effector 114 from a first position (e.g., home or resting position) to a second position and the compression spring 120 may be configured to move/pivot the end effector 114 from the second position to the first position. For example, the linear displacement of the motion block 118 imparted by the transducer 116 may urge the arm 118a to slide along the curved surface 114a along one side of the end effector 114 to pivot the end effector 114 away from the first position about the pin 124. As the end effector 114 pivots away from the first position, a distance/space between the motion block 118 and end effector 114 within which the compression spring 120 is disposed may be decreased, e.g., as the side of the end effector 114 opposite the curved surface 114a extends into the space within which the compression spring 120 is housed. The compression spring 120 may move from a substantially non-compressed configuration to a compressed configuration as the end effector 114 pivots further away from the first position (see e.g., FIG. 1C). The transducer 116 may then be de-energized and the force exerted by the compression spring 120 against the proximal end of the end effector 114 may move/return the end effector 114 from the second position to the first position about the pin 124 (see e.g., FIG. 1D). As discussed below, the continued/repeated back-and-forth in-plane reciprocation of the end effector 114 resulting from the combined/opposing forces of the compression spring 120 and transducer 116 may generate/provide high frequency oscillation (e.g., 40-60 kHz) of the distal end of the end effector 114.

Referring to FIGS. 2A-2C, in one embodiment, an ultrasonic medical device 200 of the present disclosure may include a sling 222 disposed within a distal portion of a flexible elongate sheath 210 (e.g., catheter, etc.). The sling 222 may include a reflow element 223 extending beyond a distal end of the flexible elongate sheath 210. In various embodiments, the reflow element 223 may include an outer surface configured to promote attachment of the sheath 210 to the sling 222. For example, the outer surface of reflow element 223 may include bumps and/or ridges to increase surface area and friction for combining the sheath 210 to the sling 222. In such examples, the sheath 210 may be placed over reflow element 223 and then shrunk around the sling 222 (e.g., via heat shrinking) to attach the sheath 210 to the sling 222. An end effector 214 (e.g., blade, etc.) may be pivotally attached to the reflow element 223 such that a cutting edge 214b of the end effector 214 may extend beyond a distal end of the sling 222. A transducer 216 (e.g., one or more piezoelectric stacks/disks) may be housed within the sling 222, e.g., within the portion of the sling 222 disposed within the distal portion of the flexible elongate sheath 210. A motion block 218 may be housed within the distal portion of the flexible elongate sheath 210 and between the transducer 216 and the end effector 214. An arm 218a (e.g., distal arm) of the motion block 218 may be configured to move along (e.g., slide along) a curved surface 214a of the end effector 214. In various embodiments, the curved surface 214a may be disposed along one side of a proximal portion of the end effector 214 and may extend into the distal portion of the flexible elongate sheath 210. The end effector 214 may be pivotally attached to the reflow element 223 of the sling 222 by a pin or lever arm 224 extending through opposite sides of the reflow element 223 and through a proximal portion of the end effector 214. A torsion spring 220 (e.g., pre-load device, etc.) may be disposed around an outer surface of the pin 224 within the reflow element 223. As discussed below, the torsion spring 220 may move from a substantially non-compressed (e.g., relaxed) configuration to a compressed configuration around the pin 224 as the arm 218a of the motion block 218 moves/pivots the end effector 214 away from first position (e.g., a home or resting position) to a second position.

In various embodiments, the transducer 216 and motion block 218 may be housed within the proximal portion of the sling 222, e.g., within the distal portion of the flexible elongate sheath 210. One or more leads 226 (e.g., flexible control wire(s), flexible signal wire(s), etc.) may extend along a length of the flexible elongate sheath 210 (e.g., along an inner or outer surface of the flexible elongate sheath). A proximal end of the lead(s) 226 may be connected to (e.g., conductively or electrically connected to) an external energy source (e.g., a RF generator, not shown) and a distal end of the lead(s) 226 may be conductively connected to the transducer 216.

In one embodiment, the transducer 216 (e.g., when energized by the external energy source) may be configured to translate (e.g., impart) linear motion (e.g., linear displacement, linear movement, etc.) to the motion block 218 relative to a longitudinal axis of the flexible elongate sheath 210. The arm 218a of the motion block 218 may be configured to move along the curved surface 214a of the end effector 214 to translate (e.g., impart) in-plane reciprocating movement (e.g., in-plane movement, etc.) to the end effector 214, e.g., as the pin 224 pivots/rotates within the reflow element 223. The combined interactions of the transducer 216, the motion block 218, the end effector 214, the pin 224 and the torsion spring 220 may translate axial displacement of the motion block by the transducer to in-plane reciprocation of the end effector 214. As discussed below, the interaction between the arm 218a of the motion block 218 and the curved surface 214a of the end effector 214 may provide angular displacement through varying radial lengths to amplify side-to-side in-plane displacement of the distal end of the end effector 214, e.g., to provide ultrasonic in-plane reciprocal movement.

In various embodiments, the combined interaction of the transducer 216 and motion block 218 may be configured to move/pivot the end effector 214 from a first position (e.g., a home or resting position) to a second position, and the torsion spring 220 may be configured to move/pivot the end effector 214 from the second position to the first position. For example, the linear displacement of the motion block 218 imparted by the transducer 216 may urge the arm 218a to slide along the curved surface 214a along one side of the end effector 214 to pivot the end effector 214 away from the first position about the pin 224. As the end effector 214 pivots away from the first position, the torsion spring 220 may move from a substantially non-compressed configuration to a compressed configuration around the pin 224. The transducer 216 may then be de-energized and the torsion spring 220 may return to the non-compressed configuration about the pin 224 to move/return the end effector 214 from the second position to the first position about the pin 224. As discussed below, the continued/repeated back-and-forth in-plane reciprocation of the end effector 214 resulting from the combined/opposing forces of the torsion spring 220 and transducer 216 may generate/provide high frequency oscillation (40-60 kHz) of the distal end of the end effector 214.

In various embodiments, the angular displacement through varying radial lengths provided by the combined interaction of the arm 118a, 218a of the motion block 118, 218 and the curved surface 114a, 214a of the end effector 114, 214 may eliminate the need for an amplification horn by converting the relatively small linear motion/displacement of the motion block 118, 218 to a significantly larger in-plane rotational displacement of the distal end of the end effector 114, 214 of the ultrasonic medical devices 100, 200. Referring to Table 1, in-plane rotational displacement at a distal end of an end effector (Blade Displacement) with a known length (Blade Length) may be calculated based on the linear displacement (Transducer Displacement) and degree of rotation (Rad) of the end effector using the formulas $L=RX_2$ (e.g., displacement) and $D=2R\,Cos(X_1/2)$ (e.g., rotation). An exemplary illustration of the geometric relationships of the parameters for these formulas is provided in FIG. 1B and/or FIG. 1F.

TABLE 1

True-scale blade length and blade displacement results

| Transducer Displacement (um) | Rotation (Rad) | Blade Length (mm) | Blade Displacement (um) |
|---|---|---|---|
| 10 | 0.006 | 8 | 48 |
| 10 | 0.006 | 12 | 72 |
| 20 | 0.011 | 8 | 88 |

Referring first to rotation, a transducer which imparts 20.0 μm (e.g., 0.02 mm) of linear displacement (D) and 1.0 mm of rotational movement ($X_1$), e.g., pivoting of the end effector around (or along with) the pin, may provide 0.011 rad (e.g., 0.5 degrees of rotation) as follows:

$$D=2R\,Cos(X_1/2)$$

$$0.02\text{ mm}=2R\,Cos(1.0\text{ mm}/2)$$

$$R=0.011\text{ rad}$$

Referring to displacement, an end effector with a length ($X_2$) of 8.00 mm rotating about a proximal end thereof at 0.0111 rad may impart 88.0 μm of transverse displacement (L) to the distal end of the end effector as follows:

$$L=RX_2$$

$$L=(0.011\text{ rad})(8.0\text{ mm})$$

$$L=88.0\text{ μm}$$

In various embodiments, the angular displacement through varying radial lengths may provide approximately 0.01 inches of in-plane ultrasonic reciprocation to an end effector at a frequency of approximately 40-60 kHz.

In one embodiment, an ultrasonic medical device 300 of the present disclosure may use distally actuated axial displacement to impart rotational (e.g., rotary) ultrasonic reciprocation (e.g., ultrasonic rotational movement, etc.) to an end effector without the need for a distal amplification horn. Referring to FIGS. 3A-3B, in one embodiment, an ultrasonic medical device 300 of the present disclosure may include a tubular end effector 312 disposed within a distal portion of a flexible elongate sheath 310 (e.g., catheter, etc.). A functional characteristic or shape 314 (e.g., blade, etc.) may be attached to or integrally formed with a distal end of the tubular end effector 312 such that a cutting edge 314b of the end effector 314 may extend beyond a distal end of the flexible elongate sheath 310. A transducer 316 (e.g., one or more piezoelectric stacks/disks) may be housed within the distal portion of the flexible elongate sheath 310 and proximal to the tubular end effector 312. An actuator rod 318 may be disposed within the distal portion of the flexible elongate sheath 310 and between the transducer 316 and the tubular end effector 312. A proximal end of the actuator rod 318 may abut or contact a distal end of the transducer 316. A distal end of the actuator rod 318 may include a hooked arm or peg 318a configured to move along (e.g., slide along) a curved slot 312a formed within a proximal portion of the tubular end effector 312. In various embodiments, the curved slot 312a may be formed within one side of the tubular end effector 312. In another embodiment, the curved slot may be formed within two or more sides of the tubular end effector 312, e.g., to provide additional rotational stability to the end effector. A compression spring 320 (e.g., pre-load device, etc.) may be disposed between a distal end of the transducer 316 and a proximal surface of an inner wall 310a of the flexible elongate sheath 310. As discussed below, the compression spring 320 may move from a substantially non-compressed (e.g., relaxed) configuration to a compressed configuration as the tubular end effector 312 moves/pivots from a first position (e.g., a home or resting position) to a second position.

One or more leads (not shown) may extend along a length of the flexible elongate sheath 310 (e.g., along an inner or outer surface of the flexible elongate sheath). A proximal end of the lead(s) may be connected to (e.g., conductively or electrically connected to) an external energy source (e.g., a RF generator, not shown) and a distal end of the lead(s) may be conductively connected to the transducer 316.

Figure 4A:
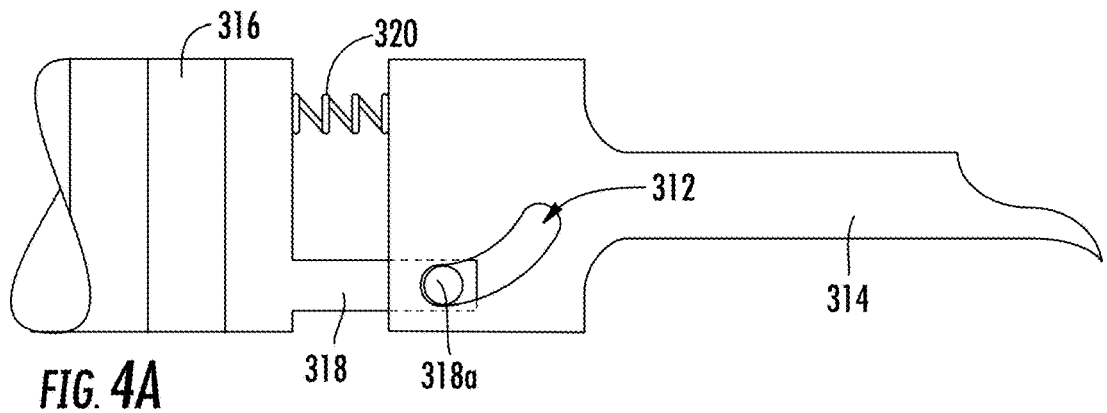
FIGS. 4A-4D provide perspective views of reciprocating motion of an end effector of the ultrasonic endoscopic medical device of FIGS. 3A-3B, according to one embodiment of the present disclosure.
Figure 4B:
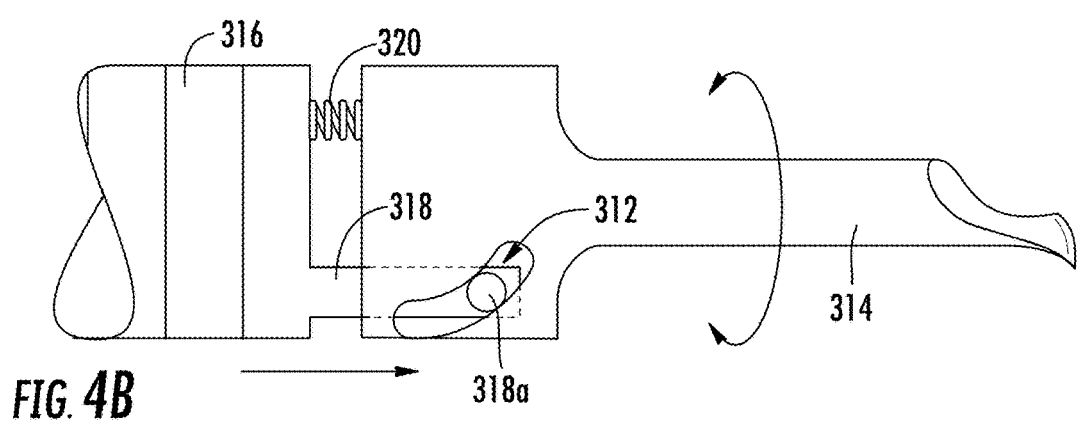
Figure 4C:
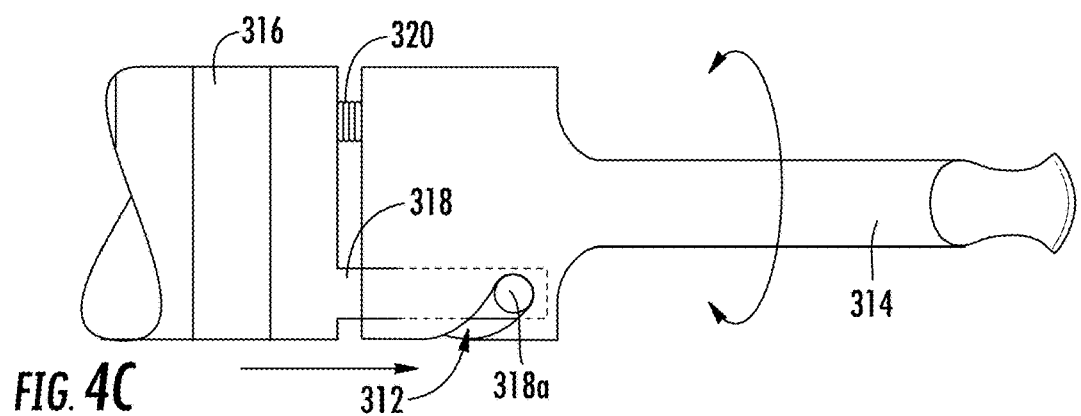
Figure 4D:
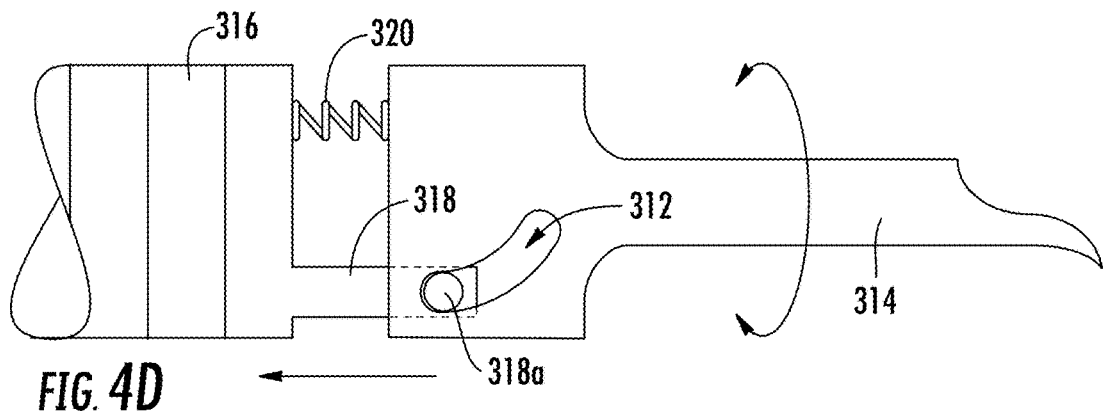

Referring to FIGS. 4A-4D, in one embodiment, the transducer 316 (e.g., when energized by the external energy source) may be configured to translate (e.g., impart) linear motion (e.g., linear displacement, linear movement, etc.) to the actuator rod 318 relative to a longitudinal axis of the flexible elongate sheath 310. The hooked arm 318a of the actuator rod 318 may be configured to move along (e.g., ride within) the curved slot 312a of the tubular end effector 312 to translate (e.g., impart) rotational reciprocation (e.g., rotary/rotational movement) to the end effector 314, e.g., as the peg 318a of the actuator rod 318 moves back and forth within/along the curved slot 312a of the tubular end effector 312. The combined interactions of the transducer 316, the actuator rod 318, the tubular end effector 312 and compression spring 320 may translate axial displacement of the actuator rod by the transducer to rotational reciprocation of the end effector 314. As discussed above, the interaction between the peg 318a of the actuator rod 318 and the curved slot 312a of the tubular end effector 312 may provide angular displacement through varying radial lengths to amplify rotational displacement of the distal end of the end effector 314, e.g., to provide ultrasonic rotational movement of the distal end of the end effector 314.

In various embodiments, the combined interaction of the transducer 316 and actuator rod 318 may be configured to move/pivot the tubular end effector 312 from a first position (e.g., home or resting position) to a second position and the compression spring 320 may be configured to move/pivot the end effector 314 from the second position to the first position. For example, the linear displacement of the actuator rod 318 imparted by the transducer 316 may urge the arm 318a to advance forward (i.e. distally to the flexible sheath 310) and cause peg 318a to slide along the curved slot 312a along one side of the tubular end effector 312 to pivot the tubular end effector 312 away from the first position. As the tubular end effector 312 pivots away from the first position, a distance/space between the transducer 316 and the wall within the flexible shaft 310 within which the compression spring 320 is disposed may be decreased. The compression spring 320 may move from a substantially non-compressed configuration to a compressed configuration as the actuator rod 318 advances and the tubular end effector 312 pivots further away from the first position. The transducer 316 may then be de-energized and the force exerted by the compression spring 320 against the proximal surface of the inner wall 310a of the flexible elongate sheath 310 may move/return the tubular end effector 312 to the first position. As discussed above, the continued/repeated back-and-forth rotary reciprocation of the end effector 314 resulting from the combined/opposing forces of the compression spring 320 and transducer 316 may generate/provide high frequency oscillation (e.g., 40-60 kHz) of the distal end of the end effector 314.

Referring to FIG. 5, in one embodiment, a transducer 116, 216, 316 of the present disclosure may include multiple piezoelectric stacks/disks a-d housed within the distal portion of a flexible elongate sheath 110, 210, 310 of the present disclosure and configured to be actuated in parallel. In various embodiments, one or more leads 126a-126d, 226a-226d (e.g., flexible control wire(s), flexible signal wire(s), etc.) may extend along a length of the flexible elongate sheath 110, 210, 310 (e.g., along an inner or outer surface of the flexible elongate sheath). A proximal end of each lead(s) 126, 226 may be connected to (e.g., conductively or electrically connected to) an external energy source (e.g., a RF generator, not shown) and a distal end of each the lead(s) 126, 226 may be conductively connected to a different one of the piezoelectric stacks/disks a-d.

In various embodiments, a distal end of an end effector 114, 214, 314 of the present disclosure may include a substantially flat/planar cutting edge 114b, 214b (e.g., as depicted in the ultrasonic medical devices 100, 200 of the present disclosure) or a curved/scalloped cutting edge 314b (e.g., as depicted in the ultrasonic medical device 300 of the present disclosure). In various additional embodiments, the end effectors 114, 214, 314 of the present disclosure may be configured to be retracted (e.g., shielded, etc.) within a distal portion of the elongate flexible sheath 110, 210, 310, e.g., for passage through a working channel of endoscope and/or advancement into a body lumen.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An ultrasonic medical device, comprising:
   a flexible elongate sheath;
   a collar attached to a distal end of the flexible elongate sheath;
   an end effector pivotally attached to the collar;
   a transducer housed within a distal portion of the flexible elongate sheath;
   a motion block housed within the distal portion of the flexible elongate sheath and between the transducer and the end effector, wherein an arm of the motion block is configured to move along a curved surface of the end effector; and
   a compression spring disposed between the motion block and a proximal end of the end effector.

2. The ultrasonic medical device of claim 1, wherein the compression spring contacts a distal end of the motion block and the proximal end of the end effector.

3. The ultrasonic medical device of claim 1, wherein the transducer is configured to translate linear motion to the motion block.

4. The ultrasonic medical device of claim 3, wherein the arm of the motion block is configured to move along the curved surface of the end effector to translate in-plane reciprocating movement to the end effector.

5. The ultrasonic medical device of claim 1, wherein the transducer is configured to move the arm of the motion block distally along the curved surface of the end effector and wherein the compression spring is configured to move the arm of the motion block proximally along the curved surface of the end effector.

6. The ultrasonic medical device of claim 1, further comprising a lead extending along a full length of the flexible elongate sheath, wherein a proximal end of the lead is connected to an energy source and a distal end of the lead is connected to the transducer.

7. The ultrasonic medical device of claim 1, wherein the transducer includes a stack of piezoelectric disks in parallel.

* * * * *